United States Patent [19]

McRae

[11] Patent Number: Plant 6,374

[45] Date of Patent: Nov. 8, 1988

[54] LILY PLANT NAMED 'SNOW KING'

[75] Inventor: Edward A. McRae, Boring, Oreg.

[73] Assignee: Melridge, Inc., Aurora, Oreg.

[21] Appl. No.: 929,323

[22] Filed: Nov. 10, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid Oriental lily having large, upright to semi-upright flowers of excellent form and long persistence both on the plant and as cut flowers, the flowers of the new plant being particularly characterized by their pure white coloration, accented by magenta spots, and by their large size and substance and their upright to semi-upright orientation. This combination is completely new in the Oriental hybrid divisions of lilies suited to forcing and to mass commercial cultivation. The plant is an excellent garden plant, highly resistant to disease, and shows tolerance of virus. The clone is vigorous and is a good grower and propagator and its bulbs may be precooled and forced for cut flower production.

1 Drawing Sheet

BACKGROUND OF THE INVENTION

My new variety of lily plant originated as a seedling which first flowered at Sandy, Oreg., in 1970 from seeds grown with the object of producing large flowered, upright and semi-upright Oriental hybrids in shades of soft pink and white suited to forcing into flower out of season, heretofore unknown in the lily breeding art. The seeds by which I achieved the desired objective resulted from my crossing the clonal variety 'Fair Lady' as the seed parent, the pollen parent being a selected form of the species *Lilium nobilissimum.* In order to cross these distantly related lilies successfully, it was necessary to maintain extremely high greenhouse temperatures for one week after pollination.

The flowers of this new lily are characterized by an upright to semi-upright orientation, extremely large size and broad tepalled, bowl-shaped form, unusually thick substance and a distinctive pure white coloration accented by magenta-rose spots, a combination unique among Oriental hybrid lilies. The new plant possesses unusually strong, stout stems with exceptionally broad leaves and its clone possesses to a high degree the desirable characteristics of hybrid vigor, great hardiness and disease resistance, possessing all of the desired characteristics of excellence of form, color and habit. Also, the clone is vigorous and a good grower and propagator as observed at Sandy, Oreg. This plant is well suited to forcing out of season when the bulbs are dug at the appropriate time and properly precooled; late October-dug bulbs, properly precooled and potted in January, will flower under glass in western Oregon, with no supplementary lighting and at moderate greenhouse temperatures, in an average of about 100 to 115 days.

My new variety of lily plant has been asexually reproduced by me and under my direction at Sandy, Oreg., and successive generations produced by natural propagation from bulblets, by bulb scale propagation, and by tissue culturing from bulb scale explants, have demonstrated that the novel and distinctive characteristics of this lily variety hold true under asexual propagation from generation to generation and appear to be firmly fixed.

DESCRIPTION OF THE DRAWING

My new variety of lily plant is illustrated in the accompanying photographic drawing which shows, in full color, a three-quarter face view of a fully opened bloom, the color rendition being as true to those specified as is reasonably possible to obtain by conventional photographic procedures.

DESCRIPTION OF THE NEW VARIETY

The following is a detailed description of my new variety of Oriental hybrid lily with nomenclature according to The International Lily Register of The Royal Horticultural Society of London, England (Second Edition, 1969), and the color designations are according to The R.H.S. Colour Chart published by The Royal Horticultural Society in 1966.

THE PLANT

Origin: Seedling.

Parentage:

*Seed parent.*—Lilium 'Fair Lady' (unpatented).

*Pollen parent.*—A selected clone of *Lilium nobilissimum,* unnamed and unpatented.

Classification:

*Horticultural.*—Division VII-B, Bowl-shaped Oriental Hybrid Lily, according to The Horticultural Classification of Lilies by The Royal Horticultural Society of London, England.

*Commercial.*—Hybrid Oriental Lily Cultivar.

Form: Single stem, erect and stately.

Height: About 70 to 125 cm., from bulbs about 14 to 18 cm. in circumference, with adequate light levels.

Growth: Vigorous and upright.

Foliage:

*Quantity.*—Abundant.

*Leaf size.*—Unusually broad, about 7 to 8 cm. wide and about 12 to 15 cm. long.

*Leaf shape.*—Lanceolate with acuminate tip.

*Texture.*—Leathery.

*Aspect.*—Glossy.

*Color.*—Medium green, lighter on the under side.

Bulbs:

*Size.*—Various, ranging to about 25 cm. in circumference in commercial use.

*Color.*—White, with flushes of soft pink or soft yellow after exposure to light.

THE BUD

Form: Long, ovoid and obtuse.

Size: About 9 to 12 cm. long and about 10 to 12 cm. in circumference just prior to opening.

Opening rate: The bud opens slowly, taking about one hour in response to morning light.

Color: White with soft green midribs.

Peduncle:

*Length.*—Averages about 4 to 6 cm., but may become longer if light levels are too low or if the bulbs have been improperly stored prior to forcing.

*Color.*—Medium green with very light plum overlay.

THE FLOWER

Blooming habit: Once annually and profusely in midseason for Oriental lilies.

Size: Large, averaging about 18 to 23 cm. in diameter, reflexing at the tips during the second day to about 15 to 18 cm. in diameter.

Borne: As a single stem racemose inflorescence having 3 to 6 flowers from a bulb about 14 to 16 cm. in circumference.

Shape: The flower forms a broad bowl shape by its second day, with the bowl being about 10 cm. deep.

Tepalage:

*Number.*—Six.

*Arrangement.*—Hexagonal and imbricated.

*Shape.*—Broad ovate with entire margins, the outer tepals being about 3 to 3.5 cm. wide and the inner tepals being about 5 to 5.5 cm. wide.

*Appearance.*—Shiny.

*Color.*—Pure white. The nectary furrows are apple green.

*Tepal spotting.*—The flowers have about 10 to 20 magenta-rose spots on each inner tepal, just above the nectaries, forming a band about 2 to 4 cm. wide surrounding the center of the flower.

*Longevity.*—The tepals stay on the stems for about 3 weeks.

Pedicel:

*Length.*—Averages about 8 to 12 cm.

*Form.*—Sturdy and ascending up to about 45° from the horizontal.

*Color.*—Medium green with very light plum overlay.

Fragrance: None.

Disease resistance: The flower and plant are resistant to disease; in particular, they are resistant to Botrytis blight and to Fusarium bulb rot.

Lasting quality: The flower is long lasting, both on the plant and as a cut flower.

THE REPRODUCTIVE ORGANS

Stamens:

*Number.*—Six.

*Arrangement.*—Typical of the genus Lilium.

*Anthers (dehisced) and pollen.*—Color: Greyed red, 179A.

*Filaments.*—Length: About 5 cm. Color: Soft green to white.

Pistils:

*Number.*—One.

*Style.*—Length: About 5 cm.

*Stigma.*—Size: Large. Color: Soft greenish white to very light pink.

Character of ovary: Characteristic of genus Lilium.

THE FRUIT

Fertility: The fruit is fertile.

Shape: Ovoid.

Color at maturity: Soft brown, sometimes overlaid with soft plum.

This new variety of Oriental hybrid lily most nearly resembles *Lilium nobilissimum,* but the new plant is taller, with stronger stems and the flowers are accented with magenta-rose spots. Also, the flowers of the new plant are not as completely upfacing as those of *L. nobilissimum,* and its flower form is more bowl-shaped and less trumpet in form.

I claim:

1. A new and distinctive variety of Oriental hybrid lily plant, substantially as herein shown and described, characterized by its unique upright to semi-upright bowl-shaped flowers of pure white coloration, accented with magenta-rose spots forming a very light and open band surrounding the flower center; and by its vigorous growth and rapid natural propagation and its versatility both as a garden plant and as a cut flower producer.

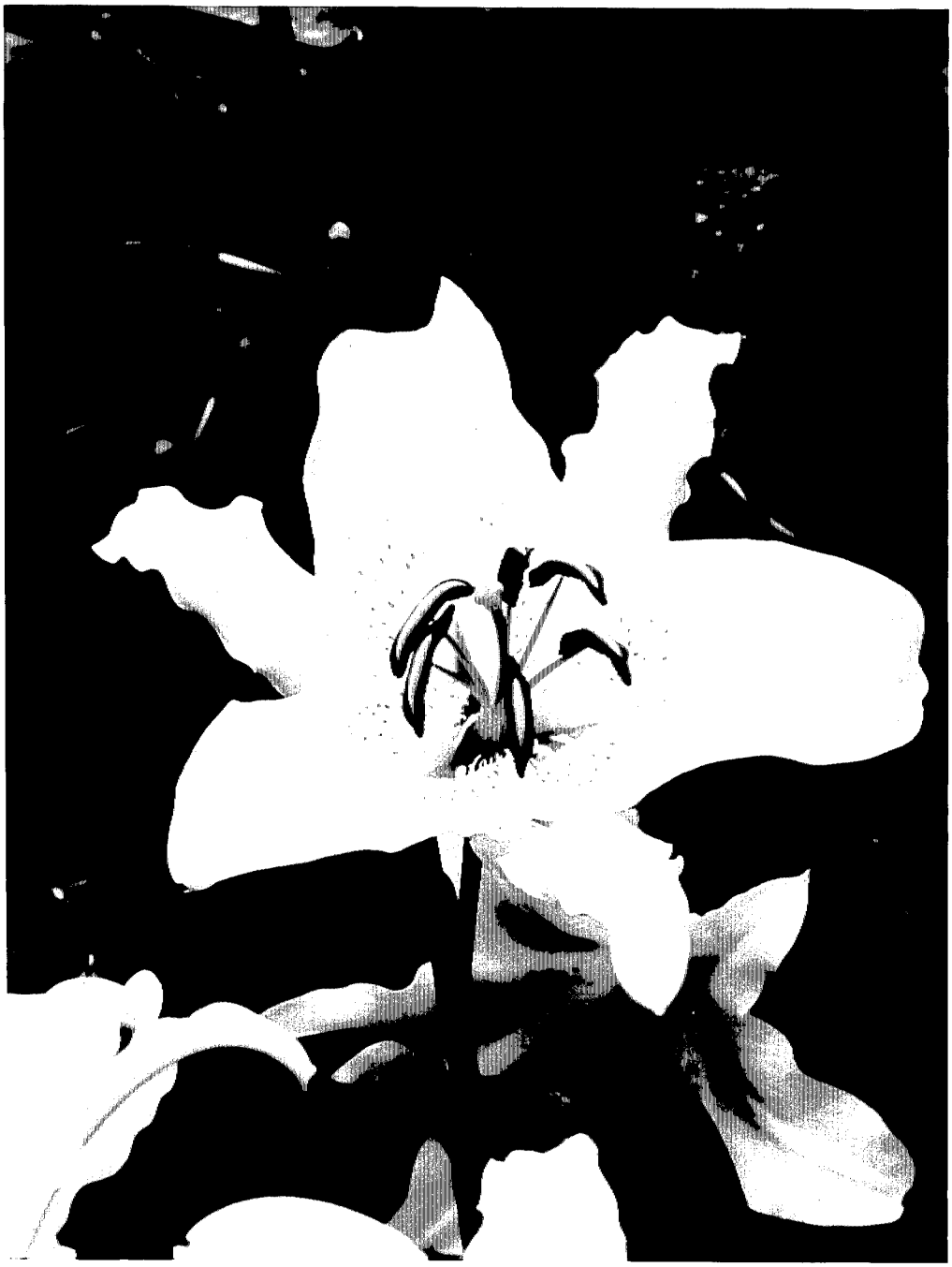

* * * * *